US012753421B2

(12) United States Patent
Shulman

(10) Patent No.: US 12,753,421 B2
(45) Date of Patent: Oct. 6, 2026

(54) METHOD FOR EMPLOYING CORN PLANT RESIDUE IN THE PRODUCTION OF DIRECT REDUCED IRON

(71) Applicant: Alvin D. Shulman, Highland Park, IL (US)

(72) Inventor: Alvin D. Shulman, Highland Park, IL (US)

( * ) Notice: Subject to any disclaimer, the term of this patent is extended or adjusted under 35 U.S.C. 154(b) by 0 days.

(21) Appl. No.: 18/235,286

(22) Filed: Aug. 17, 2023

(65) Prior Publication Data

US 2025/0059572 A1 Feb. 20, 2025

(51) Int. Cl.
*C12P 3/00* (2006.01)

(52) U.S. Cl.
CPC .................................... *C12P 3/00* (2013.01)

(58) Field of Classification Search
CPC .................................................... C12P 3/00
See application file for complete search history.

(56) References Cited

U.S. PATENT DOCUMENTS 9,127,326 B2 9/2015 Metius et al.
11,352,596 B2 6/2022 Ludtke et al.
2010/0203608 A1 8/2010 Schwarz et al.

OTHER PUBLICATIONS

Chartone et al., English machine translation of BR PI 1102449 A2, "Process of Obtaining Sponge Iron and Pig Iron", Total pp. 1-12. (Year: 2013).*
Keph et al—English Translation of UA 27018 C2—"Method for Prevention of Metal Corrosion During the Direct Reduction of Material, Which Contains Ferric Oxides (VARIANTS) and Plant for Realization the Same" (published: Feb. 28, 2000; total pp. 1-12 translation). (Year: 2000).*
Yang W-G et al., "A commercial biomass pool", CN 201762319 U (2011); PTO English translation, total pp. 1-3. (Year: 2011).*
Ludmila et al., WO 2022/104443 A1—"Sustainable agro-industrial complex for producing pig iron and co-products", Pub: May 27, 2022; Google English Machine translation attached (total pp. 1-6); (Year: 2022).*
Ahmed et al., "Effect of carbon concentration and carbon bonding type on the melting characteristics of hydrogen-reduced iron ore pellets", Journal of Materials Research and Technology, 2022, vol. 21, pp. 1760-1769. (Year: 2022).*
Zaini, et al., "Decarbonising the iron and steel industries: Production of carbon-negative direct reduced iron by using biosyngas," Energy Convers. Manage., 281:116806, pp. 1-19 (2023).
Nurdiawanti et al., "Towards fossil-free steel: Life cycle assessment of biosyngas-based direct reduced iron (DRI) production process", J. Cleaner Prod., 393:136262, pp. 1-15 (2023).
MIDREX Brochure, "MXCol: Using Syngas to makd DRI in the MIDREX Process," 8 pages (Aug. 2014).
Satyendra, "Midrex Process for Direct Reduction of Iron Ore", *ISPAT GURU* (online publication), 12 pages (Apr. 9, 2017).
Gulhane, et al., "Technical Developments in the Midrex Process", *Intl. J. of Scientific & Eng. Research*, vol. 8, Issue 5, pp. 1700-1703 (May 2017).
MIDREX Brochure, "DRI Products & Applications: Providing flexibility for steelmaking," 16 pages (Apr. 2018).
MIDREX Brochure, "The MIDREX Process—The world's most reliable and productive Direct Reduction Technology," 12 pages (Apr. 2018).
Satyendra, "Use of Direct Reduced Iron in Electric Arc Furnaces", *ISPAT GURU* (online publication), 11 pages (May 8, 2018).
Schroeder, K., "Property Reincarnation," *Ethanol Producer Magazine*, pp. 26-32 (Mar. 2022).
Schroeder K., "Verbio Grand Opening", *Ethanol Producer Magazine*, pp. 24-29 (Aug. 2022).
Lüngen et al., "History, developments and processes of direct reduction of iron ores," *8th European Coke and Iron-making Congress*, 18 pages (Sep. 1, 2022).
Home Biogas Brochure "Advantages Disadvantages," Home Biogas, Bert Yanal, Israel, 4 pages, Jan. 4, 2024.

* cited by examiner

*Primary Examiner* — Satyendra K Singh
(74) *Attorney, Agent, or Firm* — MARSHALL, GERSTEIN & BORUN LLP

(57) ABSTRACT

Direct reduced iron (DRI) is produced at a facility comprising a catalytic reformer physically associated with a vertical shaft furnace. A biogas is produced by anaerobically fermenting an annually renewable biomass, such as corn plant residue (stover). The biogas consists essentially of methane and carbon dioxide ($CH_4$+$CO_2$). The carbon dioxide is retained, and the biogas with the retained carbon dioxide is introduced into the catalytic reformer where the methane is cracked to produce carbon and gaseous hydrogen, a reducing gas ($CH4 \rightarrow C+2H_2$). The retained carbon dioxide in the biogas reacts with the carbon from the cracking step to produce carbon monoxide, another reducing gas ($C+CO_2 \rightarrow 2CO$). The two reducing gases are introduced into the vertical shaft furnace to convert iron ore to direct reduced iron. The retention of $CO_2$ in the biogas reduces the amount of recycled top-gas $CO_2$ required at the reformer.

19 Claims, 5 Drawing Sheets

METHOD FOR EMPLOYING CORN PLANT RESIDUE IN THE PRODUCTION OF DIRECT REDUCED IRON

FIELD OF INVENTION

The present invention relates generally to steel-making and more particularly to the production of direct reduced iron (DRI).

BACKGROUND OF THE INVENTION

Most of the steel currently made in the U.S.A. is made in electric arc furnaces that employ steel scrap as a feed material. A problem that arises therefrom is the presence in the scrap of tramp copper, which has an adverse effect on the quality of steel made from that scrap, limiting the products that can be made from copper-containing steel.

Copper cannot be metallurgically removed from steel, but the adverse effect of copper can be offset by diluting the concentration of copper in the molten steel in the electric arc furnace by adding thereto a feed material containing pure iron. One such material is direct reduced iron (DRI), a material made by reacting iron ore, an iron oxide, with a reducing gas at an elevated temperature below the melting point of iron ore and iron.

A brochure entitled "Midrex NG" describes a natural gas process for producing DRI, a process developed by Midrex Technologies, Inc. of Charlotte, NC, a world leader in developing DRI technology (Idem, page 3). The Midrex process employs a vertical shaft furnace into the top of which is introduced iron ore as pellets or lumps, which descend by gravity through the furnace. A combination of reducing gases, $CO+H_2$, is introduced into about the mid-point of the furnace and ascends through the descending iron ore, converting the iron ore to direct reduced iron, which is removed through the bottom of the furnace. The reducing gases are converted to $CO_2$ and $H_2O$, which are removed from the furnace as top gas.

The feed material for producing the reducing gases is natural gas, essentially methane ($CH_4$), which is introduced into a heated Midrex processing apparatus called a reformer, which is maintained at an elevated temperate at which methane cracks in the presence of a catalyst, breaking down into carbon and gaseous hydrogen ($CH_4 \rightarrow C+2H_2$). The carbon is oxidized into carbon monoxide by carbon dioxide in the furnace top gas recycled into the reformer ($C+CO_2 \rightarrow 2CO$). This is all summarized in the brochure in a generalized statement, as the reaction of $CH_4$ and $CO_2$ to produce $2H_2$ and 2CO (Id. Page 6).

The reformer is heated by fuel gas, including scrubbed top gas containing unreacted CO and $H_2$, combusted with air by burners at the reformer (Ibid. pp. 3, 5). The reducing gases are introduced into the vertical shaft furnace at an elevated temperature, which heats the iron ore and sustains the reduction reactions in the furnace but does not melt either the iron ore or the DRI.

Hot DRI discharged from the bottom of the vertical shaft furnace has the character of sponge iron. It is very porous and will reoxidize quickly. It must be cooled, and special precautions must be taken during storage and shipping. This problem can be overcome by subjecting the hot DRI to a briquetting procedure producing hot briquetted iron (HBI), which, when cooled, can be stored and shipped without special precautions. Hot DRI can be transferred directly from the vertical shaft furnace to an electric arc furnace (EAF). The mode of transfer depends upon the distance between the two furnaces. Hot DRI is introduced into the EAF at an elevated temperature, which reduces the power required to melt the DRI compared to DRI introduced at ambient temperature. This is an advantage not available with HBI, which has been stored and transported at ambient temperature after briquetting.

The Midrex NG process uses natural gas, a fossil fuel, as the basis of the reducing gas for producing DRI and as a fuel for process heat. Carbon dioxide is emitted and is not offset, unlike the carbon dioxide emitted in processing using bio-gas.

Midrex has acknowledged that there may be circumstances where natural gas should be replaced with alternative gases, most of which are fossil fuel-based and have the same disadvantages regarding carbon dioxide emission as natural gas. (Midrex brochure "DRI Products & Applications" (2018), page 12, penultimate paragraph; Midrex brochure "MXCOL" (2014), pages 2-5.)

Verbio Nevada, LLC produces, at a plant in central Iowa, a biogas having a composition essentially the same as pipeline natural gas (99% methane), using corn plant residue as the starting material. Also known as stover, corn plant residue is the corn plant material remaining in the field after the corn has been harvested and comprises stalks, cobs, leaves and husks and any part thereof. The stover is baled and transported on flat-bed semi-trailers to a processing location (a) next to an ethanol manufacturing facility that uses corn as a feed material and (b) very close to a natural gas pipeline.

At the processing location, the corn plant residue is chopped into small pieces, less than ¼ inch in size, at a hammermill, screened and mixed with water. This mixture, together with cattle manure, is introduced into a fermentation plant, where the mixture undergoes anaerobic fermentation for about 25 days. The cattle manure provides the bacteria that decomposes the corn plant residue and creates a biogas consisting essentially of methane and carbon dioxide (50-60% $CH_4$ and 40-50% $CO_2$).

The carbon dioxide is removed from the biogas by processing that produces a gas containing 99% methane, the major part of which is injected into the nearby (natural gas) pipeline for eventual consumption downstream as fuel at a power plant. A minor part of that gas is retained as fuel for boilers at the adjacent ethanol manufacturing facility.

A fermentation vat residue remaining in the fermentation vat is removed, subjected to phase separation into fermentation vat residue solid and liquid, and the solid, called humus, is spread on farm fields as organic fertilizer and soil amendment.

The Verbio biogas processing plant receives corn plant residue from corn fields within a radius of 45 miles or so from the Verbio plant. This is the distance that a semi-trailer, loaded with bales of corn plant residue and traveling at 45 miles per hour, can cover in one hour.

The Verbio plant and its operation is described in the following publications:

Schroeder, K., Property Reincarnation, Ethanol Producer Magazine, March 2022, pages 26, 30-32; and Schroeder K., Verbio Grand Opening, Ethanol Producer Magazine, August 2022, page 24.

Many, if not most, steel-making mini-mills lack commercially viable access to natural gas (either from gas fields or gas pipelines); but many mini-mills do have access to cornfields and the corn plant residue provided by these fields. As used herein, the phrase "access to cornfields" refers to corn fields within a 45-mile radius of the mini-mill.

SUMMARY OF THE INVENTION

The present invention is directed to a method that provides a mini-mill with locally produced DRI using biogas produced at a processing location associated with a direct reduction facility at the mini-mill and using locally accessed feed materials that are annually renewable and sustainable.

In essence, the present invention uses (a) the first part of the above-described Verbio process for making biogas, with modification, in combination with (b) a modification of the above-described Midrex process for making DRI. All of the equipment and processing steps employed from the Verbio process are in commercial use and commercially proven. All of the equipment employed from the Midrex process is in commercial use and commercially proven.

More particularly, the present method employs the Verbio anaerobic fermentation step and the steps preceding the fermentation step to produce a biogas consisting essentially of methane and carbon dioxide ($CH_4+CO_2$). But unlike the Verbio process, which removes the carbon dioxide from the biogas (in order to obtain 99% methane for use as pipeline gas), the present method retains the carbon dioxide in the biogas along with the methane therein. The equipment and processing steps Verbio employs to remove the $CO_2$ are eliminated along with the capital and operating expenses associated with the $CO_2$ removal.

The biogas of the present invention ($CH_4+CO_2$) is used as a replacement for the natural gas ($CH_4$ alone) employed in the Midrex process—as feed gas for the Midrex reformer. At the temperature conventionally maintained in the reformer, and in the presence of the reformer catalyst, the methane in the biogas is broken down into carbon and hydrogen gas ($CH_4 \rightarrow C+2H_2$), and importantly, the retained carbon dioxide in the biogas converts some of the carbon to carbon monoxide ($CO_2+C \rightarrow 2CO$).

The Verbio biogas reportedly contains 50-60% $CH_4$ and 40-50% $CO_2$. From a molar ratio standpoint, there is not enough $CO_2$ to convert all C resulting from the breakdown of $CH_4$, and this deficit in $CO_2$ is made up by recycling $CO_2$ from the top gas of the vertical shaft furnace, as in the Midrex process.

A principal difference between (a) the Midrex process and (b) the method of the present invention arises from the use, in (a), of natural gas (methane alone) versus the use, in (b), of a fermentation-derived biogas consisting essentially of methane plus retained carbon dioxide (e.g., 50-60% $CH_4$+ 40-50% $CO_2$). The processing in the vertical shaft furnace and downstream from there can be essentially the same in (b) as in (a).

Another difference is that, unlike the Midrex process, the present invention is not entirely dependent upon recycled top gases to form the CO reducing gas. Moreover, the employment of corn plant residue in accordance with the method of the present invention enables one to use, in the production of DRI, a gas for which the source is annually renewable by planting in successive years, with corn, the farm fields from which the corn plant residue was collected, or planting an equivalent acreage that is similarly accessible to the processing plant.

A purpose of the present invention is two-fold:

(1) Retain, for the most part, the well-established, commercially proven Midrex process and equipment currently employed at the majority of DRI processing plants; and (2) Replace the currently employed Midrex processing gas, based on a fossil fuel, ecologically disfavored in some quarters, with a processing gas based on corn plant residue, a material that is annually renewable and is widely available and accessible in those parts of the U.S.A. where most of the DRI is consumed (Midwest and South).

In addition, there is the potential for carbon credits. Not only does the present invention replace fossil fuel gas with a renewably sourced biogas, but also any $CO_2$ greenhouse gas emissions arising from the use of the biogas in the present invention are offset by the carbon dioxide absorbed from the atmosphere during the growth of the corn plant, the residue of which is the source of the biogas.

DETAILED DESCRIPTION

Figure 1:
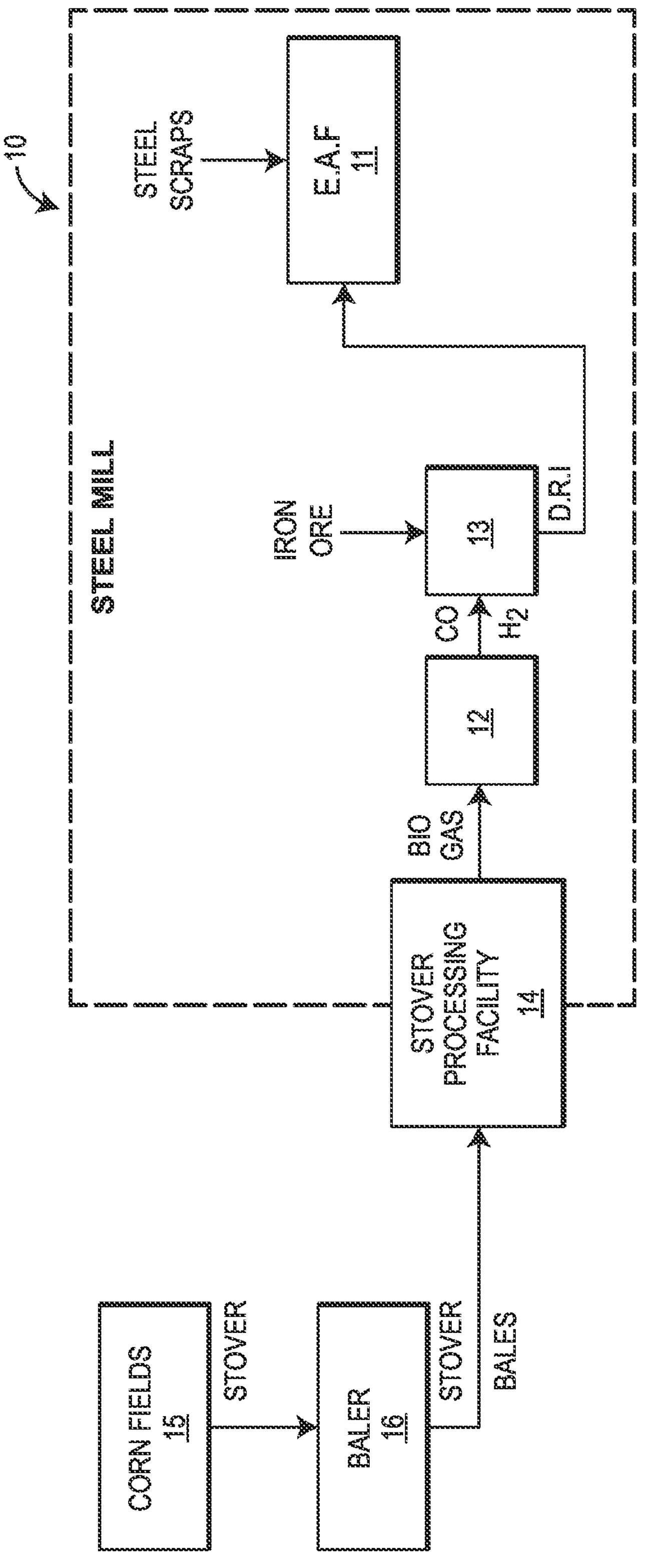
FIG. 1 is a block diagram illustrating an embodiment of a method in accordance with the present invention.

Referring initially to FIG. 1, indicated generally at 10 is a steel mill comprising an electric arc furnace (EAF) 11 and a direct reduction facility, comprising a catalytic reformer 12 and a vertical shaft furnace 13, for converting iron ore into direct reduced iron (DRI), which may be employed as feed material for electric arc furnace 11, a furnace that also receives steel scrap as a feed material.

In accordance with the present invention, there is a biomass processing facility 14 (typically processing corn stover into a biogas) that is associated with direct reduction facility 12, 13. A biomass processing facility such as 14 is associated with a direct reduction facility 12, 13 when facility 14 is connected to reformer 12 by a pipeline that transports, from facility 14 to reformer 12, a biogas consisting essentially of methane and carbon dioxide ($CH_4$+ $CO_2$), each present in double-digit percentages in the same order of magnitude.

In a preferred embodiment, steel mill 10 and its components 11-13 are physically associated with a stover processing facility 14. Two entities are deemed to be physically associated when one of them is at or next to or adjacent to the other, or if both entities are physically associated with a third entity in the manner described in the preceding part of this sentence.

The physically associated entities described in the preceding paragraph (entities 10-14) have access to a plurality of corn fields 15 that supply stover that is collected and baled by a baler 16 that produces stover bales that are loaded on flat-bed semi-trailers and transported to stover processing facility 14.

A corn field is deemed to be accessible when a semi-trailer loaded with stover bales from that field, and moving at an average speed of 45 miles per hour, can travel from that field to processing facility 14 in one hour.

A farm field further than 45 miles from processing facility 14 is deemed to be accessible if the cost of transporting stover bales from the more distant field, or from a collection site, is reasonably competitive with the cost of transporting stover bales from the 45-mile field.

Figure 2:
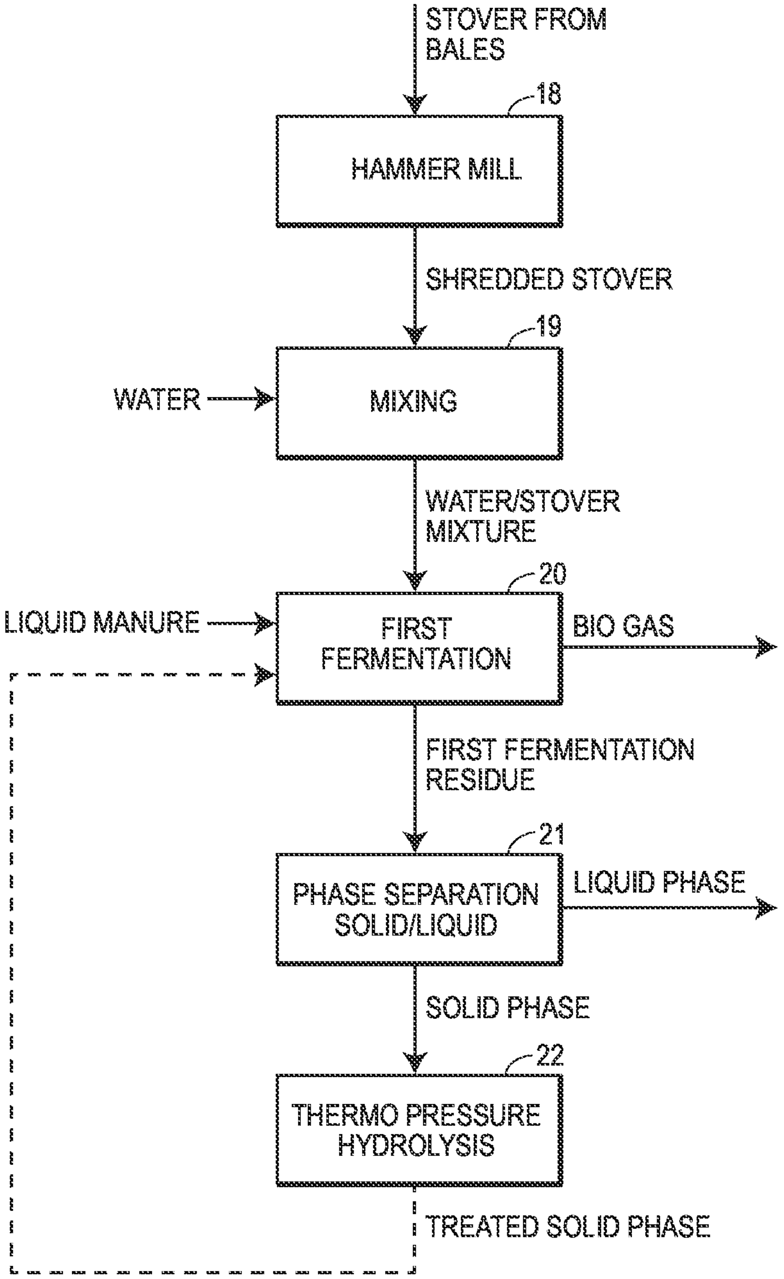
FIGS. 2 and 3 are block diagrams illustrating a stover processing procedure of the method.
Figure 3:
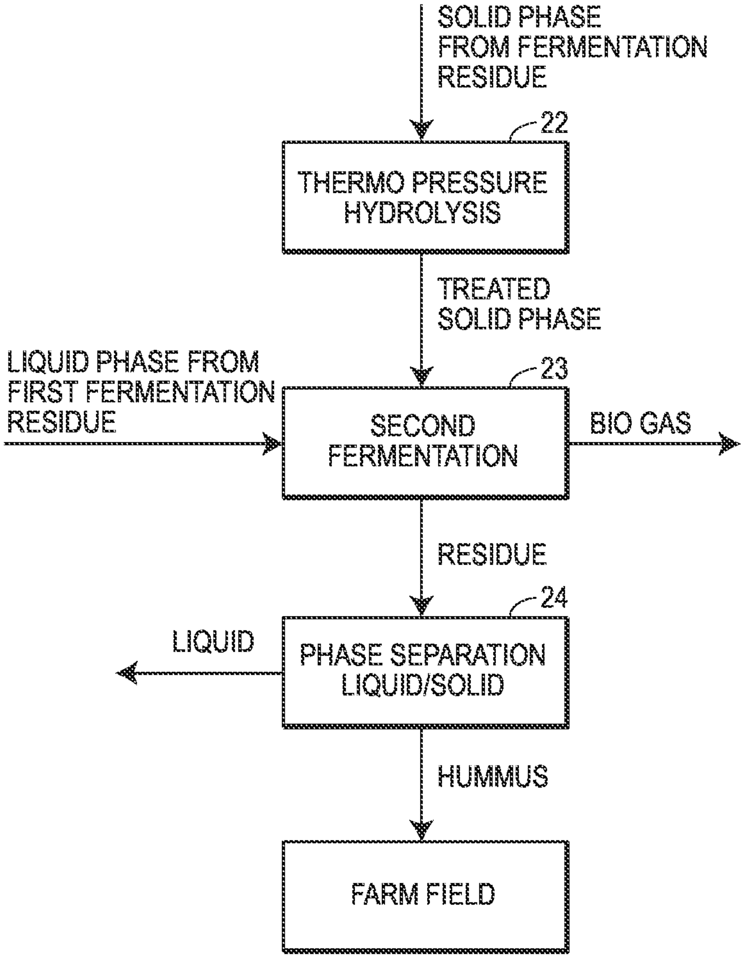

FIGS. 2 and 3 illustrate the stover processing performed at facility 14. Much of this is based on the disclosure in Schwarz et al. U.S. Application Publication No. 2010/0203608 A1, and the totality of the disclosure therein is incorporated herein by reference.

Referring initially to FIG. 2, stover from the stover bales is shredded in a hammer mill 18 and screened to a particle size no greater than about ¼ inch (about 6 mm). The shredded stover is then mixed with water at a mixing stage 19, and the mixture, together with liquid manure, is introduced into a fermentation vat 20, where anaerobic (absence of oxygen) fermentation is conducted for an average retention time of 25 days. The liquid manure provides the bacteria that activates the fermentation process. At the end of the retention time, about 40% of the organic starting materials have been degraded and converted to biogas (methane plus carbon dioxide).

Large proportions of the stover starting material are composed of cellulose, hemicellulose and lignin, which are relatively difficult to degrade and convert to biogas absent the application of external expedients to intensify degradation. Many such expedients are known to those skilled in the art, and some of them are discussed in Schwarz et al. [0005]-[0021]. One such expedient employed in accordance with an embodiment of the present invention is thermopressure hydrolysis, discussed later below.

At the end of the retention time, vat 20 contains a fermentation residue composed essentially of undegraded solid starting material, microorganisms and water. The residue is removed from vat 20 and subjected to phase separation at 21, e.g., by centrifugation or pressing, to produce a liquid phase containing (i) the water and the microorganisms and (ii) a solid phase. The solid phase represents approximately 20% to 30% of the volume of the fermentation residue from vat 20 and contains essentially the gas-forming potential still available.

The solid phase is subjected to thermopressure hydrolysis at 22. This procedure comprises heating the solid phase at a temperature in the range 170° C.-250° C. at a pressure in the range 1 MPa-4 MPa for a time in the range 10 minutes-120 minutes. Other details are contained in Schwarz et al. at [0029]-[0034] and [0045]. In accordance with the present invention, the source of heat energy for the thermopressure hydrolysis is excess, unrecycled top gas from vertical shaft furnace 13 (to be discussed below).

As a result of undergoing the thermopressure hydrolysis, the cellulose, hemicellulose and lignin, in the solid phase of the fermentation residue, are broken down and made accessible to further conversion to biogas in a subsequent anaerobic fermentation step.

The subsequent anaerobic fermentation step can be performed in a second fermentation vat shown at 23 in FIG. 3, a vat into which is also introduced the liquid phase from the fermentation residue of first fermentation vat 20, a liquid phase that was separated from the solid phase of the residue at 21. This liquid phase also contains the microorganisms from vat 20, microorganisms that will activate the fermentation process in vat 23.

Alternatively, the solid phase that has undergone thermopressure hydrolysis can be recycled back to first vat 20, in a batch process fermentation step, along with the liquid phase from the phase separation at 21. The second fermentation step occurs for 20 days, and the total degree of degradation of the organic material is 80% for the two fermentation steps.

After the second fermentation step at vat 23 (or vat 20), the fermentation residue is separated into (i) a liquid phase and (ii) a solid phase composed of spent material called digestate or hummus, which can be spread on farm fields as a fertilizer or a soil amendment.

The biogas generated at stover processing facility 14 consists essentially of 25%-50% carbon dioxide ($CO_2$) and 50%-75% methane ($CH_4$), e.g., 55% methane and 45% carbon dioxide. Unlike the biogas produced by Verbio Nevada, the carbon dioxide in the biogas of the present invention is not removed from the biogas. There is retained, in the biogas directed to the direct reduction facility 12, 13, at least a major part (and preferably all) of the carbon dioxide generated at stover processing facility 14. Also, unlike the Verbio Nevada biogas production process, there is no consumption of a major part of the biogas, at a location physically unassociated with steel mill 10, for a purpose unrelated to the direct reduction of iron. Instead, the totality of the biogas is directed to direct reduction facility 12, 13 without there having been removed any of the carbon dioxide generated at stover processing facility 14.

Figure 4:
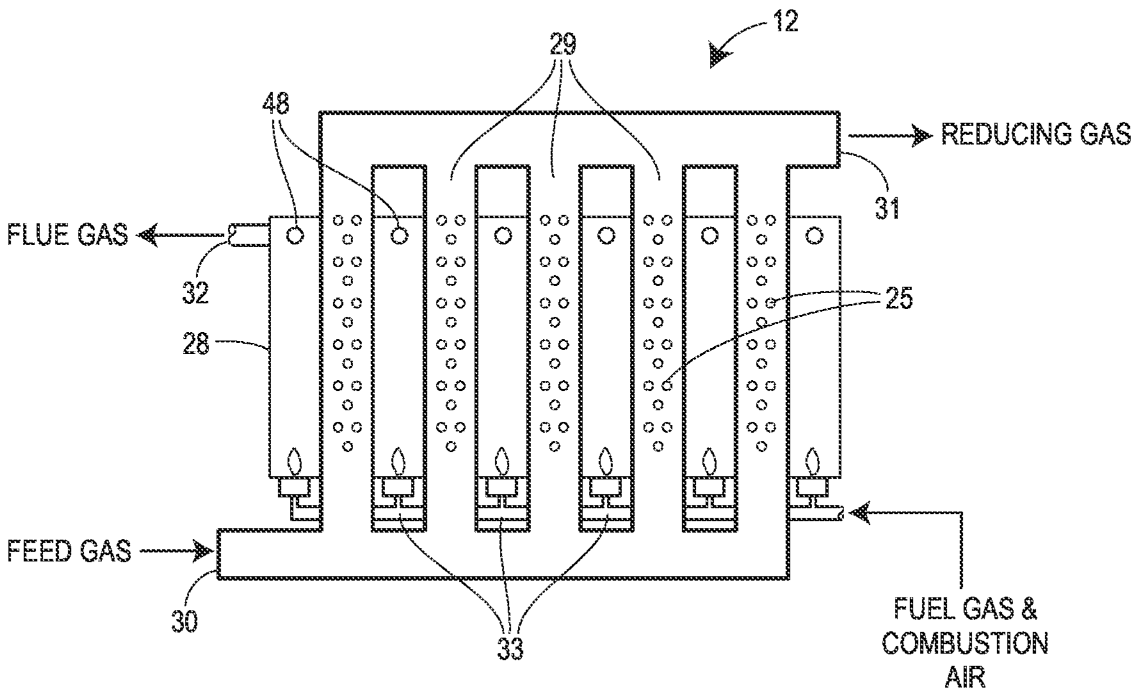
FIGS. 4 and 5 are diagrammatic representations of equipment employed in the production of direct reduced iron in accordance with the present invention.
Figure 5:
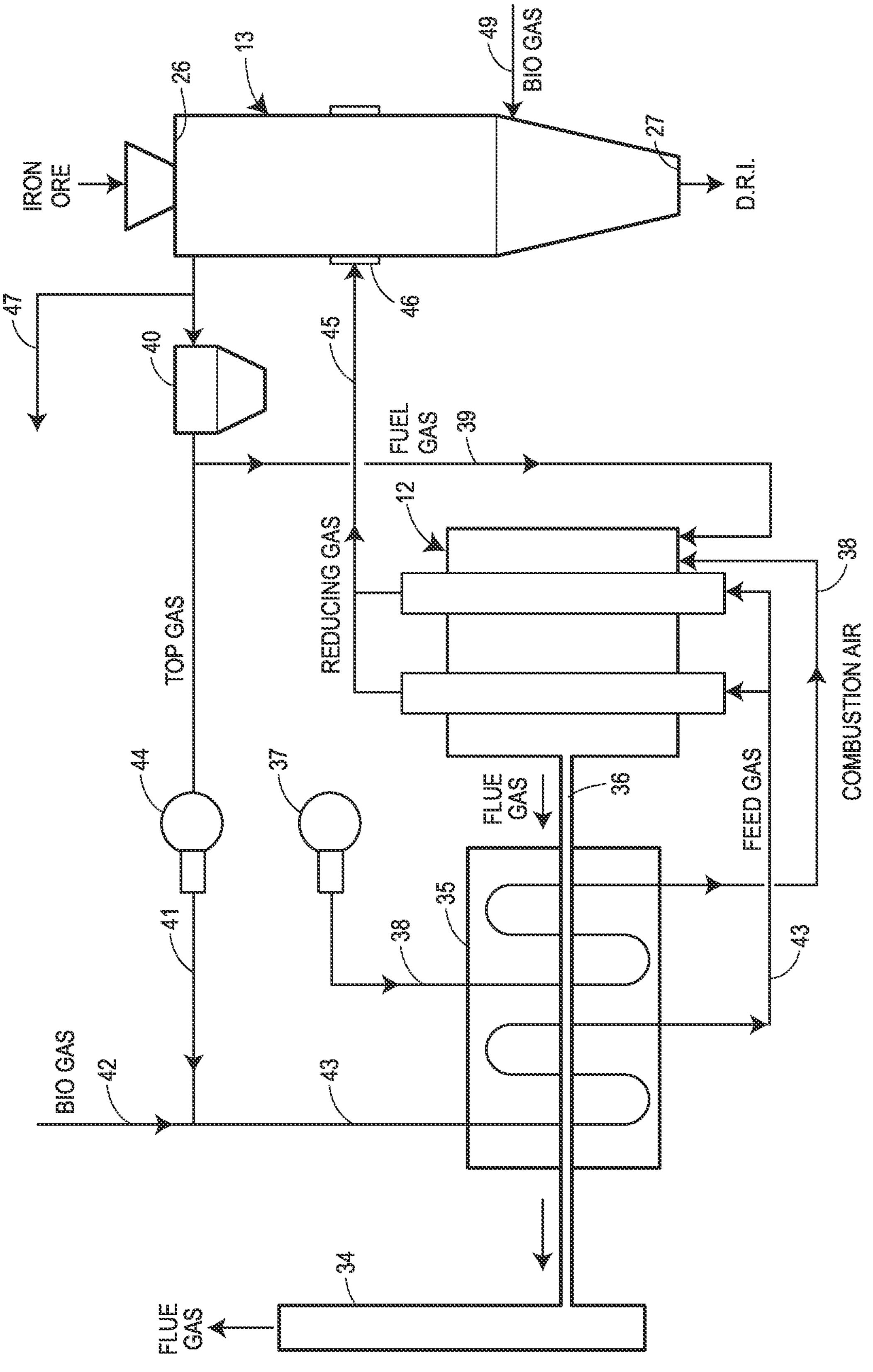

FIGS. 4-5, concern the direct reduction facility that is employed in the performance of the present method and that comprises catalytic reformer 12 and vertical shaft furnace 13, both constituting commercially proven equipment, as supplied by Midrex. The operations performed at the direct reduction facility are discussed in detail in one or more of the following publications, all or portions of which are incorporated herein by reference:

Lüngen et al., History, developments and processes of direct reduction of iron ores, $8^{th}$ European Coke and Iron-making Congress, September 2022 (pages 4-5);

Midrex brochure, "Midrex NG," April 2018 (all);

Satyendra, Midrex Process for Direct Reduction of Iron Ore, Ispat Guru, Apr. 9, 2017, ispatguru.com (all);

Gulhane, et al., Technical Developments in the Midrex Process, Intl. J. of Scientific & Eng. Resch., Vol. 8, Issue 5, May 2017 (all); and Satyendra, Use of Direct Reduced Iron in Electric Arc Furnaces, Ispat Guru, May 8, 2013 (all).

Referring to FIG. 4, reformer 12 comprises a box 28 containing a multiplicity of catalyst tubes 29, each containing catalytic material 25. Reformer box 28 comprises an inlet 30 for receiving feed gas and an outlet 31 for emitting hot reducing gas produced in reformer 12. A heating arrangement 33 receives fuel gas and combustion air to heat box 28 and its contents. Flue gas produced by heating arrangement 33 is expelled from box 28 at flue gas outlet 32.

Catalytic material 25 normally comprises (a) nickel (sometimes cobalt), as the active ingredient to speed up the reactions in reformer 12, and (b) an alumina or magnesia carrier that gives the catalytic material its strength and shape.

Referring now to FIG. 5, biogas from stover processing facility 14 (FIG. 1) is directed through a biogas line 42 into a reformer feed line 43, which carries feed gas through a heat-recovery system 35, where the feed gas is preheated before entering reformer box 28 at inlet 30 (FIG. 4). As previously noted, the biogas in the feed gas consists essentially of methane and retained carbon dioxide.

Reformer box 28 is heated to, e.g., about 1000° C. The contents of reformer box 28, including catalytic material 25, are heated by heating arrangement 33 to an elevated temperature, e.g., 900° C. In reformer 12, some of the methane in the biogas is reacted with the retained carbon dioxide in the biogas, at the elevated temperature in the reformer, in the presence of the nickel catalyst, to reform that methane and produce a reducing gas comprising carbon monoxide and gaseous hydrogen ($CO+H_2$). The reforming of the methane is performed upstream of, and apart from, vertical shaft furnace 13.

The reducing gas is discharged from reformer 12 at outlet 31 (FIG. 4) into a line 45, which directs the reducing gas, at a temperature in the range, e.g., 850° C.-1000° C. into vertical shaft furnace 13 at bustle 46 located between upper and lower furnace ends 26, 27, respectively.

The retained carbon dioxide in the biogas is less than the stoichiometric amount required to react with all the methane in the biogas. The methane in the biogas that is unreformed, by the carbon dioxide in the biogas, undergoes reforming with carbon dioxide from another source, as discussed more fully below.

Vertical shaft furnace 13 includes four zones. There is a reducing zone that extends upwardly from bustle 46, where the reducing gas has been introduced, and a heating zone extending downwardly from upper furnace end 26 toward the reducing zone. Extending downwardly from the reducing zone is a transition zone, and below the transition zone is a cooling zone extending upwardly from lower furnace end 27 toward the transition zone.

The reducing gas is introduced into furnace 13 at a temperature in the range, e.g., 950° C.-1000° C. and heats furnace 13 and its contents. Iron ore in pellet and/or lump form is introduced into furnace 13 at upper end 26 and descends through furnace 13 under the urging of gravity, while hot reducing gas introduced at bustle 46 rises through the descending iron ore, which has been converted by the reducing gas to direct reduced iron that is removed from furnace 13 at lower end 27. The temperature in furnace 13 is below the melting point of both iron ore and direct reduced iron.

The conversion reactions between the reducing gas ($CO+H_2$) and the iron ore ($Fe_2O_3$) produce, as reaction product gases, carbon dioxide ($CO_2$) and water vapor ($H_2O$), which are removed from furnace 13 as top gas, which also includes some unreacted reducing gas (CO and $H_2$).

Some of the top gas is directed through a recycle line 41 into reformer feed gas line 43, where it joins the biogas. The recycled top gas is then conducted through heat-recovery system 35, where the recycled top gas is preheated. The preheated, recycled top gas is then directed into reformer 12, where methane in the biogas, unreformed by the retained carbon dioxide in the biogas, is reformed by reacting with the carbon dioxide in the recycled top gas, at an elevated temperature, in the presence of a catalyst (the nickel in tubes 25 (FIG. 4)) to produce additional reducing gas for introduction into vertical shaft furnace 13. The methane in the biogas that is reformed by the retained carbon dioxide in the biogas, and the methane in the biogas that is reformed by the carbon dioxide in the recycled top gas, are intermixed in the reformer and undergo concurrent reforming by carbon dioxide. All of the methane in the reformer originates at biomass processing facility 14. (FIG. 1).

The carbon dioxide in the top gas recycled into reformer 12 is less than the totality of the carbon dioxide introduced into the reformer. The biogas introduced into the reformer provides the reformer with carbon dioxide independent of the carbon dioxide provided to the reformer by the recycled top gas. As previously noted, the biogas that is received in the reformer comprises at least a major part of the carbon dioxide produced in the biogas at stover processing facility 14 (FIG. 1). Preferably, the biogas is received at the reformer without there having been removed from the biogas any part of the carbon dioxide produced at stover processing facility 14.

The top gas leaving furnace 13 is processed at a scrubber 40. Part of the scrubbed gas is employed as a fuel for reformer 12, to which the fuel is directed by fuel gas line 39. The fuel gas, together with preheated combustion air, is combusted at burner arrangement 33 of reformer 12 (FIG. 4). A combustion air blower 37 directs combustion air, via a line 38, through heat-recovery system 35 to preheat the combustion air. Hot combustion product gas (flue gas) is circulated through reformer 12 via flues 48, and is removed from reformer 12 through flue gas outlet 32 and conducted by flue gas conduit 36 through heat-recovery system 35, where the heat from the flue gas is employed to preheat the combustion air in line 38 and the biogas and recycled top gas in line 43. Spent flue gas is removed from the direct reduction facility through an ejector stack 34 communicating with flue gas conduit 36.

There are four options for delivering direct reduced iron (DRI) discharged from lower end 27 of shaft furnace 13. These options are: cold DRI, hot briquetted iron (HBI), hot DRI delivered directly to electric arc furnace 11 through a gravity feed system or through a hot transport conveyor or a hot DRI transport vessel. These options are illustrated diagrammatically in Satyendra (2017) in FIG. 2, "Midrex process flow sheet," at the third page therein, and they are described at the sixth page therein, all of which have been incorporated previously herein by reference.

DRI is typically discharged at lower end 24 of furnace 13 at a temperature of about 400° C., a temperature that reflects cooling conducted in the cooling zone of furnace 13 by the introduction of cooling gas at ambient temperature (e.g., unheated biogas). When DRI is to be delivered directly to the electric arc furnace (EAF), the higher the delivery temperature, the less electric power required to melt the DRI at the EAF.

As previously noted, some of the methane in the biogas introduced into reformer 12 is reformed there into reducing gas by the retained carbon dioxide in that biogas. The methane in the biogas that is unreformed by the $CO_2$ in the biogas, and that undergoes reforming, is reformed by carbon dioxide in the recycled top gas. The amount (a) of recycled top gas required to complete the reforming of the methane in the reformer, when the methane is part of a biogas also containing retained carbon dioxide, is less than (b) the amount of recycled top gas required to reform the same amount of methane when the methane is unaccompanied by retained carbon dioxide.

The difference between (a) and (b) is (c) excess unrecycled top gas that has an elevated temperature up to 400° C., which is the temperature of the top gas as initially discharged from furnace 13.

As previously noted, the recycled top gas (line 41) and the top gas employed as fuel for reformer 12 (line 39) are scrubbed at scrubber 40. The excess, unrecycled top gas is unscrubbed and uncooled, and as such, it is available for use as a heating medium. To this end, the excess, unrecycled top gas is directed, via line 47 located upstream of scrubber 40, for use as process heat for the thermopressure hydrolysis 22 performed at stover processing facility 14 (see FIGS. 2-3), when facility 14 is physically associated with the direct reduction facility.

Thus, a biogas containing both methane and carbon dioxide in accordance with the present invention has heat energy advantages. The presence of the $CO_2$ in the biogas itself frees up top gas containing the same amount of $CO_2$, at a temperature up to 400° C., for use as a heating medium in the direct reduction facility or elsewhere in the steel mill or at the biomass processing facility when that facility is physically associated with the direct reduction facility.

Optimum productivity for the direct reduction process is achieved by maximizing the temperature of the furnace burden (iron ore undergoing conversion to DRI) and maximizing the quality of the reducing gas introduced into the furnace. The temperature of the furnace burden is maximized by increasing the temperature of the reducing gas (currently above 900° C.-1000° C.) (See Lüngen, et al. (2022) page 5), and the quality of the reducing gas is increased by increasing the CO and $H_2$ contents. Various procedures and expedients for doing both are described in Satyendra (2017), at pages 7-8, previously incorporated herein by reference. The composition of the various DRIs produced at furnace 13 are detailed in Satyendra (2017), $9^{th}$ page. DRI is predominantly elemental iron (Fe) with up to about 4% carbon (C), and there is some oxygen present as iron oxide (FeO). The carbon in DRI can be combined with iron, as cementite ($Fe_3C$), or the carbon can be present as solid, elemental, uncombined carbon. Metallized iron, the total of elemental iron and cementite, is preferably in the range 94%-96% of the DRI when the DRI is used as a feed material at an electric arc furnace (Satyendra, 2013, page 3).

About two-thirds of the carbon in DRI is present in combined form ($Fe_3C$) (Ibid page 4), which is preferable to uncombined carbon. The carbon in DRI performs a function during steel-making in an EAF, reacting with the FeO in the molten steel to reduce the oxygen content of the steel. $Fe_3C$ is a stable compound, but elemental carbon can be lost to combustion in the EAF atmosphere (Idem.). In addition, $Fe_3C$ dissolves in the steel bath and dissociates therein in an exothermic reaction yielding energy in the process whereas the dissolution of uncombined carbon in the steel bath is endothermic. (Ibid, page 5).

The carbon content of DRI can be increased by injecting natural gas (methane ($CH_4$)) into the transition zone of the vertical shaft furnace. The heat in the transition zone, together with the iron particles there (a catalyst), cracks the methane ($CH_4 \rightarrow C+2H_2$) and deposits uncombined carbon in the DRI. The $H_2$ released by the cracking flows upwardly, providing additional reduction (Satyendra, 2017, pages 8, 18).

In the present invention, natural gas ($CH_4$) is replaced by biogas ($CH_4+CO_2$), and the biogas reacts with the carbon from the cracked methane ($CH_4$) to produce carbon monoxide ($CO_2+C \rightarrow 2CO$), which reacts with the iron in the DRI to produce cementite ($3Fe+2CO \rightarrow Fe_3C+CO_2$), an exothermic reaction. (Satyendra, 2017, page 4). The biogas is introduced into the transition zone via line 49 (FIG. 5).

There is not enough $CO_2$ in the biogas to react with all the carbon from the cracked methane of the biogas, so there is deposition of unreacted carbon in the DRI, as well as cementite, when biogas is injected in the transition zone. In contrast, the injection of natural gas (methane without carbon dioxide) deposits only unreacted carbon in the DRI (Satyendra, 2017, supra, page 8).

Midrex has developed a procedure for increasing the carbon content of the DRI up to 4% with 85%-90% of the carbon combined as cementite ($Fe_3C$). (Lüngen, page 5) Carbon monoxide made in the Midrex reformer is added to the transition zone with the natural gas. The carbon monoxide reacts with iron in the DRI, and the heat from the resulting exothermic reaction is used to produce additional carbon (via methane cracking ($CH_4 \rightarrow C+2H_2$) without sacrificing temperature (Idem.) The carbon monoxide from the Midrex reformer is mixed with gaseous hydrogen ($CO+H_2$) as the CO leaves the reformer, and the two gases have to be separated before the CO is injected into the transition zone.

The introduction, into the transition zone, of biogas containing retained carbon dioxide, in accordance with the present invention, enables one to provide the DRI with cementite using internally generated carbon monoxide. As previously noted, the carbon dioxide in the biogas reacts with the carbon from the cracked methane to produce carbon monoxide ($CH_4 \rightarrow C+H_2$; $CO_2+C \rightarrow 2CO$).

This reduces the amount of externally generated, reformer-produced carbon monoxide required to provide a predetermined amount of cementite and decreases the amount of reducing gases ($CO+H_2$) diverted from introduction into the reduction zone of the vertical shaft furnace.

In the Midrex process, as described in Satyendra (2017), unheated natural gas is introduced into the transition zone. This has a cooling effect, which limits the amount of natural gas that can be introduced there. Preheating the natural gas allows larger amounts of gas to be employed, which would produce more carbon in the direct reduced iron (either as $Fe_3C$ or as solid carbon) and a higher DRI production rate, all without the quenching effect of unheated natural gas. Preheating is being explored, per Satyendra (Idem., page 8).

In accordance with the present invention, the biogas introduced into the transition zone is preheated using, as a heating medium, the excess unrecycled gas, uncooled and unscrubbed, as removed from the vertical shaft furnace at a temperature of up to 400° C. Heat transfer is produced using, e.g., a conventional gas-to-gas heat exchanger (not shown).

DRI undergoes cooling when unheated gas is introduced into the transition and cooling zones, per conventional practice. In such cases, DRI is discharged from the lower end of the vertical shaft furnace at a temperature of about 400° C. When DRI is to be delivered directly to a physically associated electric arc furnace, the DRI is cooled less, if at all, and is desirably discharged at a temperature in the range of 600° C.-700° C. The higher the discharge temperature, the less electrical energy required to heat the DRI to a temperature above its melting point. Preheating the biogas introduced into the transition zone of the vertical shaft furnace contributes to a higher discharge temperature.

The present invention is directed to the use of biogas made from biomass. A preferred form of biomass is grain plant residue.

Corn is a grain. The corn plant residue (stover) is a grain plant residue. The present invention is applicable to grain plant residues, generally, as well as other forms of biomass. The discussion herein has been primarily in the context of corn plant residue because corn fields are the grain fields most readily accessible in the areas of the U.S. where most mini-mills are located and where most of the DRI is consumed (Midwest and South). Other relevant grains include rye, oats, barley, wheat and the like.

What is claimed is:

1. A method of employing biogas in the production of direct reduced iron (DRI), said method comprising the steps of:

providing an iron-making plant having a direct reduction facility, for producing DRI, and comprising a catalytic reformer and a vertical shaft furnace that receives iron ore and emits a top gas comprising (i) carbon dioxide ($CO_2$) and (ii) unreacted carbon monoxide (CO) and gaseous hydrogen ($H_2$);

providing a biogas that has been formed from corn plant residue at a biogas processing facility that is located upstream of said reformer, said biogas consisting essentially of methane ($CH_4$) and carbon dioxide, each being present in double-digit percentages;

retaining at least a major part of the carbon dioxide present in said biogas;

introducing said biogas with the retained carbon dioxide into said reformer, for use there as processing gas and as one of a plurality of sources of carbon dioxide employed there, there being no provision for the removal of said carbon dioxide from said biogas;

introducing, into said reformer, top gas comprising carbon dioxide;

reacting, in said reformer, the methane from said biogas with (a) the retained carbon dioxide from said biogas and (b) the carbon dioxide from said top gas, to produce a biosyngas comprising carbon monoxide and gaseous hydrogen ($CH_4+CO_2\rightarrow 2CO+2H_2$); and introducing said biosyngas into said vertical shaft furnace for use as reducing gas to convert said iron ore to iron and produce DRI.

2. A method as recited in claim 1 wherein said retaining step retains substantially all the carbon dioxide that is in the biogas produced at said biogas processing facility.

3. A method as recited in claim 1 wherein said vertical shaft furnace comprises, in descending order from an upper end, a heating zone, a reducing zone, and a transition zone, and said method further comprises:

introducing iron ore into said vertical shaft furnace at said upper end;

introducing reducing gas into said reducing zone;

converting said iron ore to direct reduced iron (DRI) as the iron ore descends through said vertical shaft furnace, by gravity, to produce DRI at said transition zone;

and increasing the carbon monoxide (CO) content in said transition zone by introducing into the transition zone a gas consisting essentially of said biogas ($CH_4+CO_2$) with said retained $CO_2$ and producing internally generated CO there;

there being no natural gas introduced into said transition zone;

the introduction, into said transition zone, of said biogas resulting in a plurality of reactions culminating in an exothermic reaction between (a) carbon monoxide, internally generated within said transition zone, and (b) iron from said DRI.

4. A method as recited in claim 3 and comprising:

increasing the carbon monoxide content in said transition zone in accordance with at least one of the following expedients (a) and (b):

(a) doing so without introducing, into said transition zone, carbon monoxide produced at said reformer;

(b) doing so without introducing, into said transition zone, carbon monoxide produced outside said transition zone.

5. A method as recited in claim 4 and comprising:

introducing said biogas, consisting essentially of methane and carbon dioxide, into said transition zone;

providing said transition zone with a temperature at which methane breaks down, in the presence of a catalyst, into carbon and gaseous hydrogen ($CH_4\rightarrow+C+2H_2$);

providing said transition zone with a catalyst in the form of iron from said DRI;

and, in said transition zone, reacting carbon dioxide from said biogas with the carbon from the breakdown of said methane, to produce internally generated carbon monoxide in said transition zone ($C+CO_2\rightarrow 2CO$).

6. A method of employing biogas in the production of direct reduced iron (DRI), said method comprising the steps of:

providing a biogas processing facility that is (a) accessible to a plurality of corn plant fields that provide corn plant residue and is (b) located upstream of and physically associated with an iron-making plant that is accessible to said plurality of corn plant fields and has a direct reduction facility for producing DRI and that comprises (i) a catalytic reformer for producing biosyngas comprising carbon monoxide and gaseous hydrogen ($CO+H_2$) from biogas and (ii) a vertical shaft furnace that employs said biosyngas as a reducing gas to convert iron ore to DRI and that emits a top gas comprising carbon dioxide;

subjecting said corn plant residue to processing at said biogas processing facility to form, upstream of said reformer, biogas consisting essentially of methane ($CH_4$) and carbon dioxide ($CO_2$), each being present in double digit percentages;

retaining at least a major part of said carbon dioxide present in said biogas; and directing said biogas, with the retained carbon dioxide, for use at said reformer as one of a plurality of sources of carbon dioxide employed there to produce biosyngas for use as the reducing gas to convert said iron ore into iron and produce DRI, there being no provision for the removal of said carbon dioxide from said biogas.

7. A method as recited in any one of claim 1 or 6 wherein:

there is no fossil material employed as a feed ingredient in the above-recited method;

all of the methane ($CH_4$) introduced into said method originates at said biogas processing facility; and substantially all of the top gas containing $CO_2$ introduced into said method is introduced upstream of said reformer.

8. A method of employing biogas in the production of direct reduced iron (DRI), said method comprising the steps of:

providing an iron-making plant having a direct reduction facility, for producing DRI, and comprising a catalytic reformer and a vertical shaft furnace that receives iron ore and emits a top gas comprising carbon dioxide ($CO_2$);

providing a biogas that has been produced from corn plant residue at a biogas processing facility that is located upstream of said reformer, said biogas consisting essentially of methane ($CH_4$) and carbon dioxide, each being present in double-digit percentages;

retaining at least a major part of the carbon dioxide present in said biogas;

introducing said biogas with the retained carbon dioxide into said reformer, for use there;

there being no provision for the removal of said retained $CO_2$ from said biogas;

reacting, in said reformer, the methane from said biogas with the retained carbon dioxide from said biogas to produce a biosyngas comprising carbon monoxide and gaseous hydrogen ($CH_4+CO_2\rightarrow 2CO+2H_2$);

introducing said biosyngas into said vertical shaft furnace for use as reducing gas to convert said iron ore to iron and produce DRI;

said vertical shaft furnace comprising, in descending order, from an upper end, a heating zone, a reducing zone and a transition zone, and said method further comprises:

introducing iron ore into said vertical shaft furnace at said upper end;

introducing reducing gas into said reducing zone;

converting said iron ore to DRI as the iron ore descends through said vertical shaft furnace, by gravity, to produce DRI at said transition zone;

providing said transition zone with a temperature at which methane breaks down, in the presence of a catalyst, into carbon and gaseous hydrogen ($CH_4 \rightarrow C+2H_2$);

providing said transition zone with a catalyst in the form of iron from said DRI; and internally generating carbon monoxide (CO) at said transition zone by introducing, into the transition zone, said biogas with the retained $CO_2$.

9. A method as recited in claim 8 wherein:

no natural gas is introduced into said transition zone;

the introduction, into said transition zone, of said biogas resulting in a plurality of reaction culminating in an exothermic reaction between (a) carbon monoxide, internally generated within said transition zone, and (b) iron from said DRI.

10. A method as recited in claim 8 and comprising:

Internally generating said carbon monoxide in said transition zone in accordance with at least one of the following expedients (a) and (b):

(a) doing so without introducing, into said transition zone, carbon monoxide produced at said reformer;

(b) doing so without introducing, into said transition zone, carbon monoxide produced outside said transition zone.

11. A method as recited in claim 10 and comprising:

introducing said biogas, consisting essentially of methane and carbon dioxide, into said transition zone;

and, in said transition zone, reacting (a) carbon dioxide from said biogas with (b) the carbon from the breakdown of said methane, to produce internally generated carbon monoxide in said transition zone ($C+CO_2 \rightarrow 2CO$).

12. A method of employing biogas in the production of direct reduced iron (DRI), said method comprising the steps of:

providing a biogas that has been produced from corn plant residue at a biogas processing facility, the biogas consisting essentially of methane and carbon dioxide ($CH_4+CO_2$), each being present in double-digit percentages;

providing a direct reduction facility comprising a catalytic reformer physically associated with a vertical shaft furnace having an upper end and comprising in descending order from said upper end, a heating zone, a reducing zone, a transition zone and a cooling zone;

retaining at least a major part of the carbon dioxide present in said biogas;

there being no provision for the removal of said retained $CO_2$ from said biogas;

introducing said biogas into said catalytic reformer;

producing biosyngas comprising carbon monoxide and gaseous hydrogen ($CO+H_2$) in said reformer;

introducing iron ore into said vertical shaft furnace at its upper end;

introducing said biosyngas, as a reducing gas, into the reducing zone of said vertical shaft furnace;

converting said iron ore to iron as the iron ore descends, by gravity, through said vertical shaft furnace, to produce direct reduced iron (DRI) in the transition zone;

providing said transition zone with a temperature at which methane breaks down, in the presence of a catalyst, into carbon and gaseous hydrogen ($CH_4 \rightarrow C+2H_2$);

providing said transition zone with a catalyst in the form of iron from said DRI; and internally generating carbon monoxide (CO) at said transition zone by introducing, into the transition zone, said biogas with the retained carbon dioxide ($CO_2$).

13. A method as recited in claim 12 and comprising:

Internally generating carbon monoxide in said transition zone in accordance with at least one of the following expedients (a) and (b):

(a) doing so without introducing, into said transition zone, carbon monoxide produced at said reformer;

(b) doing so without introducing, into said transition zone, carbon monoxide produced outside said transition zone.

14. A method as recited in claim 12 and comprising:

introducing said biogas, consisting essentially of methane and said retained carbon dioxide, into said transition zone;

and, in said transition zone, reacting the retained carbon dioxide from said biogas with the carbon from the breakdown of said methane, to produce internally generated carbon monoxide in said transition zone ($C+CO_2 \rightarrow 2CO$).

15. A method as recited in claim 12 and further comprising:

internally generating carbon monoxide at said transition zone by introducing, into said transition zone, said biogas with the retained carbon dioxide;

there being no natural gas introduced into said transition zone;

the introduction, into said transition zone, of said biogas resulting in a plurality of reactions culminating in an exothermic reaction between (a) carbon monoxide internally generated within said transition zone, and (b) iron from said DRI.

16. A method as recited in any one of claim 3 or 8 or 12 and comprising:

providing an electric arc furnace in physical association with said vertical shaft furnace;

reacting said internally generated carbon monoxide (CO) with iron (Fe) from the DRI in the transition zone, in an exothermic reaction;

removing DRI from the vertical shaft furnace;

and delivering the DRI, removed from the vertical shaft furnace, directly to said electric arc furnace for use there as feedstock.

17. In a method for producing direct reduced iron (DRI) employing a direct reduction facility comprising a catalytic reformer physically associated with a vertical shaft furnace having upper and lower ends and, in descending order from said upper end, a heating zone, a reducing zone, a transition zone and a cooling zone, wherein said method comprises the steps of:

introducing, into said catalytic reformer, a biogas produced from corn plant residue at a biogas processing facility, the biogas consisting essentially of methane and carbon dioxide ($CH_4+CO_2$), each being present in double-digit percentages;

retaining at least a major part of the carbon dioxide present in said biogas;

there being no provision for the removal of said retained $CO_2$ from said biogas;

converting said biogas to biosyngas comprising carbon monoxide and gaseous hydrogen ($CO+H_2$) in said reformer;

providing said transition zone with a temperature at which methane breaks down, in the presence of a catalyst, into carbon and gaseous hydrogen ($CH_4 \rightarrow C+2H_2$);

providing said transition zone with a catalyst in the form of iron from said DRI;

introducing said biosyngas into the reducing zone of said vertical shaft furnace, for use as a reducing gas;

introducing iron ore into said vertical shaft furnace at its upper end; and converting said iron ore to iron as the iron ore descends, by gravity, through said vertical shaft furnace to produce direct reduced iron (DRI) at said transition zone;

the improvement comprising a process for generating carbon monoxide (CO) internally, in said transition zone, by introducing, into said transition zone, a gas consisting essentially of said biogas with the retained carbon dioxide.

18. A method as recited in claim 17 wherein:

the carbon monoxide generated internally in the transition zone reacts there with iron from the DRI in an exothermic reaction to provide cementite ($Fe_3C$) as well as heat and additional $CO_2$ there.

19. A method as recited in any one of claim 8 or 12 or 17 wherein:

said retaining step comprises retaining substantially all of the $CO_2$ that was in said biogas when the biogas was formed at the biogas processing facility.

* * * * *